United States Patent
Lupia et al.

(10) Patent No.: US 7,309,682 B2
(45) Date of Patent: Dec. 18, 2007

(54) STABILIZED BODY CARE PRODUCTS, HOUSEHOLD PRODUCTS, TEXTILES AND FABRICS

(75) Inventors: Joseph A. Lupia, Colfax, NC (US); Joseph Suhadolnik, Yorktown Heights, NY (US); Mervin G. Wood, Mobile, AL (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 462 days.

(21) Appl. No.: 10/970,112

(22) Filed: Oct. 21, 2004

(65) Prior Publication Data

US 2005/0186170 A1    Aug. 25, 2005

Related U.S. Application Data

(60) Provisional application No. 60/515,889, filed on Oct. 30, 2003.

(51) Int. Cl.
     *C11D 7/26*      (2006.01)
     *C11D 7/32*      (2006.01)
     *C11D 7/60*      (2006.01)

(52) U.S. Cl. ............... 510/119; 510/130; 510/137; 510/275; 510/276; 510/499; 510/500; 8/405; 424/49; 424/65; 424/69; 424/70.1; 424/401

(58) Field of Classification Search ............ None
See application file for complete search history.

(56) References Cited

U.S. PATENT DOCUMENTS

| 4,898,901 A | 2/1990 | Ravichandran et al. ..... 524/237 |
| 5,081,300 A | 1/1992 | Odorisio et al. ............ 564/297 |
| 5,844,029 A | 12/1998 | Prabhu et al. .............. 524/236 |
| 5,922,794 A | 7/1999 | Prabhu et al. .............. 524/236 |
| 6,362,152 B1 * | 3/2002 | Young et al. ................ 510/386 |
| 6,368,358 B1 * | 4/2002 | Glenn et al. ................. 8/115.6 |
| 6,599,326 B1 | 7/2003 | Seltzer et al. .................. 8/101 |
| 6,831,048 B2 * | 12/2004 | Kezuka et al. ............. 510/175 |
| 2005/0054549 A1 * | 3/2005 | Kezuka et al. ............. 510/407 |

FOREIGN PATENT DOCUMENTS

| WO | 00/25730 | 5/2000 |
| WO | 00/25731 | 5/2000 |
| WO | 01/07550 | 2/2001 |
| WO | WO01/81525 | * 4/2001 |

* cited by examiner

*Primary Examiner*—Gregory R. Del Cotto
(74) *Attorney, Agent, or Firm*—Mervin G. Wood

(57) ABSTRACT

Disclosed are stabilized body care products, household products, textiles and fabrics which comprise certain dialkylhydroxyamine stabilizers, dialkylhydroxylamine stabilizer salts, nitrone stabilizers or amine oxide stabilizers. Dyed products and articles are effectively stabilized against color degradation. The products are for example skin-care products, hair-care products, dentifrices, cosmetics, laundry detergents and fabric softeners, non-detergent based fabric care products, household cleaners and textile-care products.

14 Claims, No Drawings

STABILIZED BODY CARE PRODUCTS, HOUSEHOLD PRODUCTS, TEXTILES AND FABRICS

This application claims benefit under 35 USC 119(e) of U.S. provisional application No. 60/515,889, filed Oct. 30, 2003.

The present invention relates to the use of selected dialkylhydroxylamine stabilizers, dialkylhydroxylamine stabilizer salts, nitrone stabilizers or amine oxide stabilizers for the protection of body care products, household products, textiles and fabrics against the deleterious effects of light, heat and oxygen.

The stabilized compositions for example comprise dyes that are stabilized against color change.

WO 00/25730 and WO 00/25731 are aimed at the stabilization of body care and household products.

WO 01/07550 teaches the treatment of fabric with hindered amine stabilizers.

U.S. Pat. No. 6,599,326 teaches the stabilization of pulp or paper with dialkylhydroxylamines or substituted dialkylhydroxylamines or their salts.

U.S. Pat. No. 4,898,901 discloses nitrone stabilizers.

U.S. Pat. Nos. 5,081,300, 5,844,029 and 5,922,794 disclose amine oxide stabilizers.

DETAILED DISCLOSURE

The present invention pertains to a stabilized composition comprising
(a) a body care product, household product, textile or fabric and
(b) an effective stabilizing amount of at least one compound selected from the group consisting of
   (i) the dialkylhydroxylamine stabilizers,
   (ii) the dialkylhydroxylamine stabilizer salts,
   (iii) the nitrone stabilizers and
   (iv) the amine oxide stabilizers.

Dialkylhydroxylamine stabilizers, for example N,N,-dialkylhydroxylamines and N,N-dibenzylhydroxylamine, are well known as useful stabilizers for a variety of polymeric substrates as is taught for example in U.S. Pat. Nos. 4,590,231, 4,668,721, 4,782,105, 4,876,300 and 5,013,510, the relevant parts of which are incorporated herein by reference.

U.S. Pat. Nos. 4,649,221 and 4,703,073 teach the use of polyhydroxylamine compounds and alkylated N,N-dibenzylhydroxylamine derivatives, respectively, towards stabilizing polyolefins. The disclosures of these U.S. patents are also hereby incorporated by reference.

Ester, amide or thio substituted N,N-dialkylhydroxylamines are described in U.S. Pat. Nos. 4,612,393, 4,720,517 and 5,019,285, the relevant disclosures of which are also hereby incorporated by reference.

For example, the present dialkylhydroxylamine stabilizers are those disclosed in the above mentioned U.S. Patents, and are for instance of the formula $R_1R_2N\text{—OH}$ where
$R_1$ is alkyl of 1 to 36 carbon atoms, cycloalkyl of 5 to 12 carbon atoms or aralkyl of 7 to 9 carbon atoms; or $R_1$ is said alkyl, cycloalkyl or aralkyl substituted by one to six alkyl of 1 to 12 carbon atoms, halogen, cyano, $E_1O$—, $E_1CO$—, $E_1OCO$—, $E_1COO$—, $E_1S$—, $E_1SO$—, $E_1SO_2$—, —$NH_2$, —$NHE_1$, —$NE_1E_2$, —$PO(OE_1)(OE_2)$ or —$OPO(OE_1)(OE_2)$ groups;

$R_2$ is hydrogen or independently has the same meaning as $R_1$, where at least one of $R_1$ and $R_2$ contains a hydrogen alpha to the —NOH moiety; or $R_1$ and $R_2$ together form a $C_{2-12}$ heterocyclic ring which contains at least one carbon substituted hydrogen alpha to the —NOH moiety, where said $C_{2-12}$ heterocyclic ring is unsubstituted or is substituted by one to three three alkyl of 1 to 12 carbon atoms, halogen, cyano, $E_1O$—, $E_1CO$—, $E_1OCO$—, $E_1COO$—, $E_1S$—, $E_1SO$—, $E_1SO_2$—, —$NH_2$, —$NHE_1$, —$NE_1E_2$, —$PO(OE_1)(OE_2)$ or —$OPO(OE_1)(OE_2)$ groups; or where said $C_{2-12}$ heterocyclic ring is interrupted by one to three —O—, —$NE_1$—, —CO—, —$CONE_1$-, —S—, —SO—, —$SO_2$—, —COO—, —$PO_3$— or —$PO_4E_1$ groups; or where said heterocyclic ring is both substituted and interrupted by said groups; and $E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500.

The phrase "where at least one of $R_1$ and $R_2$ contains a hydrogen alpha to the —NOH moiety" means that the present dialkylhydroxylamines are not di-tert-alkylhydroxylamines.

The present dialkylhydroxylamine stabilizers are, for example, N,N-dihydrocarbylhydroxylamines wherein $R_1$ and $R_2$ are independently benzyl, methyl, ethyl, octyl, lauryl, dodecyl, tetradecyl, hexadecyl, heptadecyl or octadecyl, or wherein $R_1$ and $R_2$ are each the alkyl mixture found in hydrogenated tallow amine.

The present dialkylhydroxylamine stabilizers are, for example, N,N-dihydrocarbylhydroxylamines selected from the group consisting of N,N-dibenzylhydroxylamine, N,N-dimethylhydroxylamine, N,N-diethylhydroxylamine, N,N-bis(2-hydroxypropyl)hydroxyl-amine, N,N-bis(3-hydroxypropyl)hydroxylamine, N,N-bis(2-carboxyethyl)hydroxylamine, N,N-bis(benzylthiomethyl)hydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine, N,N-di(hydrogenated tallow)hydroxylamine,

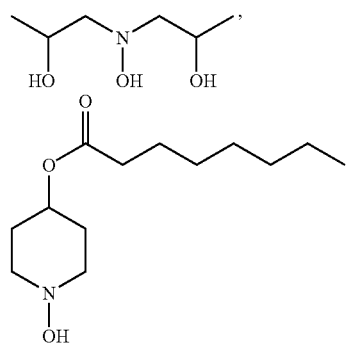

and

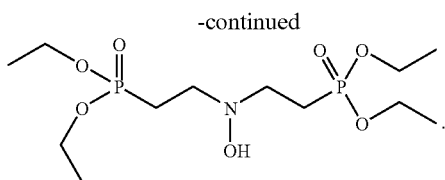

For example, the present dialkyihydroxylamine stabilizers are N,N-diethylhydroxylamine, N,N-bis(2-hydroxypropyl)hydroxylamine, N,N-bis(3-hydroxypropyl)hydroxylamine or N,N-dibenzylhydroxylamine or the N,N-di(alkyl)hydroxylamine produced by the direct oxidation of N,N-di (hydrogenated tallow)amine. The last named dialkylhydroxylamine, that is N,N-di(hydrogenated tallow) hydroxylamine, is as prepared in the working Examples of U.S. Pat. No. 5,013,510.

The dialkylhydroxylamine stabilizer salts are inorganic or organic acid salts of the present dialkylhydroxylamine stabilizers. For example, the dialkylhydroxylamine stabilizer salts are of the formula

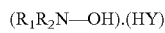

$(R_1R_2N-OH).(HY)$ where $R_1$ and $R_2$ are as defined for the dialkylhydroxylamine stabilizers, and HY is an inorganic or organic acid.

For example, Y is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid (NTA), diethylenetriaminepentamethylenephosphonic acid (DTPMPA), hydroxyethylethylenediamine-triacetic acid (HEDTA), ethylenediaminetetraacetic acid (EDTA), diethylenetriaminepentaacetic acid (DTPA), diethylenediaminetetraacetic acid or of diethylenetriaminepentaacetic acid, an alkylsulfonate or an arylsulfonate.

For instance, when HY is hydrochloric acid, Y is chloride and the dialkylhydroxylamine salt is a dialkylhydroxylammonium chloride salt.

For example, Y is chloride, bisulfate, sulfate, phosphate, nitrate, ascorbate, formate, acetate, benzoate, oxalate, citrate, a carboxylate of ethylenediaminetetraacetic acid or of diethylenetriaminepentaacetic acid or polyacrylate, for instance Y is chloride, bisulfate or citrate.

For example, the present dialkylhydroxylamine stabilizer salts are salts of the specific dialkylhydroxylamine stabilizers disclosed above.

For example, the present dialkylhydroxylamine stabilizer salts are tris(N,N-diethylhydroxylammonium) citrate or tris (N,N-dibenzylhydroxylammonium) citrate.

The nitrone stabilizers may be for example those as described in U.S. Pat. No. 4,898,901, which is hereby incorporated by reference.

The nitrone stabilizers are for example of the formula

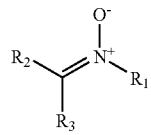

wherein $R_1$ is alkyl of 1 to 36 carbon atoms, cycloalkyl of 5 to 12 carbon atoms or aralkyl of 7 to 9 carbon atoms; or R1 is said alkyl, cycloalkyl or aralkyl substituted by one to six alkyl of 1 to 12 carbon atoms, halogen, cyano, $E_1O-$, $E_1CO-$, $E_1OCO-$, $E_1COO-$, $E_1S-$, $E_1SO-$, $E_1SO_2-$, $-NH_2$, $-NHE_1$, $-NE_1E_2$, $-PO(OE_1)(OE_2)$ or $-OPO(OE_1)(OE_2)$ groups;

$R_2$ is hydrogen or independently has the same meaning as $R_1$; or $R_1$ and $R_2$ together form a $C_{2-12}$ heterocyclic ring which is unsubstituted or is substituted by one to three three alkyl of 1 to 12 carbon atoms, halogen, cyano, $E_1O-$, $E_1CO-$, $E_1OCO-$, $E_1COO-$, $E_1S-$, $E_1SO-$, $E_1SO_2-$, $-NH_2$, $-NHE_1$, $-NE_1E_2$, $-PO(OE_1)(OE_2)$ or $-OPO(OE_1)(OE_2)$ groups; or where said $C_{2-12}$ heterocyclic ring is interrupted by one to three $-O-$, $-NE_1-$, $-CO-$, $-CONE_1-$, $-S-$, $-SO-$, $-SO_2-$, $-COO-$, $-PO_3-$ or $-PO_4E_1$ groups; or where said heterocyclic ring is both substituted and interrupted by said groups;

$E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500; and $R_3$ independently has the same meaning as $R_1$.

The nitrone stabilizers may be the corresponding oxidation products of the dialkylhydroxylamine stabilizers. That is to say, the nitrone stabilizers may be nitrone analogues of the present dialkylhydroxylamine stabilizers. The nitrone stabilizers are for example, N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecyinitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-di (hydrogenated tallow)hydroxylamine.

The amine oxide stabilizers are for example those disclosed in U.S. Pat. Nos. 5,081,300, 5,162,408, 5,844,029, 5,880,191 and 5,922,794, the relevant parts of each incorporated herein by reference.

The amine oxide stabilizers are for example saturated tertiary amine oxides as represented by the formula:

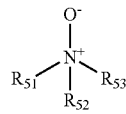

wherein $R_1$ is alkyl of 1 to 36 carbon atoms, cycloalkyl of 5 to 12 carbon atoms or aralkyl of 7 to 9 carbon atoms; or $R_1$ is said alkyl, cycloalkyl or aralkyl substituted by one to six alkyl of 1 to 12 carbon atoms, halogen, cyano, $E_1O$—, $E_1CO$—, $E_1OCO$—, $E_1COO$—, $E_1S$—, $E_1SO$—, $E_1SO_2$—, —$NH_2$, —$NHE_1$, —$NE_1E_2$, —$PO(OE_1)(OE_2)$ or —$OPO(OE_1)(OE_2)$ groups;

$R_2$ is hydrogen or independently has the same meaning as $R_1$; or $R_1$ and $R_2$ together form a $C_{2-12}$ heterocyclic ring which is unsubstituted or is substituted by one to three three alkyl of 1 to 12 carbon atoms, halogen, cyano, $E_1O$—, $E_1CO$—, $E_1OCO$—, $E_1COO$—, $E_1S$—, $E_1SO$—, $E_1SO_2$—, —$NH_2$, —$NHE_1$, —$NE_1E_2$, —$PO(OE_1)(OE_2)$ or —$OPO(OE_1)(OE_2)$ groups; or where said $C_{2-12}$ heterocyclic ring is interrupted by one to three —O—, —$NE_1$-, —CO—, —$CONE_1$-, —S—, —SO—, —$SO_2$—, —COO—, —$PO_3$— or —$PO_4E_1$ groups; or where said heterocyclic ring is both substituted and interrupted by said groups;

$E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500; and $R_3$ independently has the same meaning as $R_1$;

wherein at least one of $R_1$, $R_2$ and $R_3$ contains a β carbon-hydrogen bond.

Examples of amine oxide stabilizers are where $R_1$ and $R_2$ are independently benzyl or substituted benzyl. It is also possible for each of $R_1$, $R_2$, and $R_3$ to be the same residue. $R_1$ and $R_2$ may also independently be alkyl groups of 8 to 26 carbon atoms, for example alkyl groups of 10 to 26 carbon atoms. $R_3$ may be an alkyl group of 1 to 22 carbon atoms, for example methyl or substituted methyl. Also, the present amine oxides include those wherein $R_1$, $R_2$, and $R_3$ are the same alkyl groups of 6 to 36 carbon atoms.

The amine oxide stabilizer is for example Genox™ EP, a di($C_{16}$-$C_{18}$)alkyl methyl amine oxide, CAS# 204933-93-7.

Alkyl groups, including alkyl groups of the various substituent groups, are linear or are branched.

Alkyl is for example methyl, ethyl, propyl such as n- or isopropyl, butyl such as n-, iso-, sec- and tert-butyl, pentyl, hexyl, heptyl, octyl, nonyl, decyl, undecyl, dodecyl, tridecyl, tetradecyl, pentadecyl, hexadecyl, heptadecyl or octadecyl.

Aryl is $C_6$-$C_{12}$aryl, for example phenyl or naphthyl.

Cycloalkyl is for example, cyclopentyl, cyclohexyl, cycloheptyl, cyclooctyl, cyclononyl, cyclodecyl, cycloundecyl or cyclododecyl.

Aralkyl is for example phenylalkyl, which is alkyl substituted by phenyl. Examples are benzyl, α-methylbenzyl, and α-cumyl.

Alkenyl is ethylenically unsaturated alkyl, for example allyl, ethenyl, propenyl, butenyl.

Alkyl groups substituted by hydroxy are for example hydroxyethyl, di-hydroxyethyl, hydroxypropyl, di-hydroxypropyl, hydroxybutyl, hydroxypentyl or hydroxyhexyl.

Halogen is for example chloro, fluoro or bromo.

$C_{2-12}$ heterocyclic rings are for example 5- or 6-membered rings such as

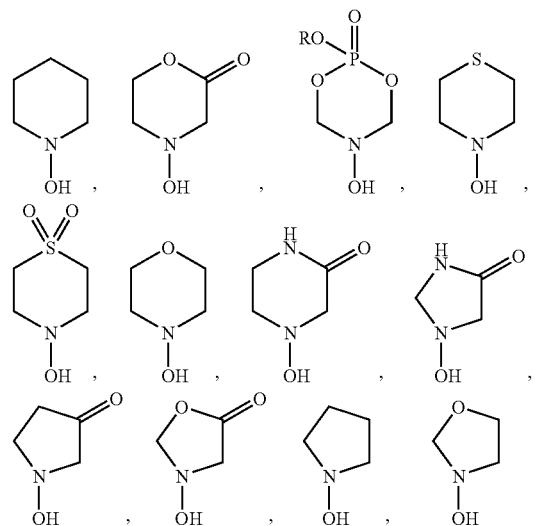

and the like.

The present compositions may comprise further traditional additives, for example ultraviolet (UV) light absorbers and antioxidants.

Accordingly, the present invention further pertains to a stabilized composition comprising (a) a body care product, household product, textile or fabric, (b) an effective stabilizing amount of at least one compound selected from the group consisting of
  (i) the dialkylhydroxylamine stabilizers,
  (ii) the dialkylhydroxylamine stabilizer salts,
  (iii) the nitrone stabilizers and
  (iv) the amine oxide stabilizers and (c) at least one compound selected from the group consisting of the ultraviolet light absorbers, antioxidants, tocopherol, tocopherol acetate, hindered amine light stabilizers, complex formers, optical brighteners, surfactants and polyorganosiloxanes.

The additional additives of present component (c) are for example those disclosed in co-pending U.S. application Ser. No. 09/830,788, filed May 1, 2001 and Ser. No. 09/830,787, filed May 1, 2001. The disclosures of these co-pending applications are hereby incorporated by reference. These applications are published as WO 00/25730 and WO 00/25731.

The UV (ultraviolet light) absorbers are for example selected from group consisting of the 2H-benzotriazoles, the s-triazines, the benzophenones, the α-cyanoacrylates, the oxanilides, the benzoxazinones, the benzoates and the α-alkyl cinnamates.

The UV absorbers are for example 2,4,6-tris(2-hydroxy-4-octyloxyphenyl)-1,3,5-triazine;

2-(2,4-dihydroxyphenyl)-4,6-bis(2,4-dimethylphenyl)-1,3,5-triazine;

2,4-bis(2-hydroxy-4-propyloxyphenyl)-6-(2,4-dimethylphenyl)-1,3,5-triazine;

2-(2-hydroxy-4-octyloxyphenyl)-4,6-bis(4-methylphenyl)-1,3,5-triazine;

2-(2-hydroxy-4-dodecyloxyphenyl)-4,6-bis(2,4-dimethylphenyl)-1,3,5-triazine;

2-[2-hydroxy-4-(2-hydroxy-3-butyloxypropyloxy)phenyl]-4,6-bis(2,4-dimethylphenyl)-1,3,5-triazine;

2-[2-hydroxy-4-(2-hydroxy-3-octyloxypropyloxy)phenyl]-4,6-bis(2,4-dimethylphenyl)-1,3,5-triazine;

2-[2-hydroxy-4-(2-hydroxy-3-tridecyloxy-propyloxy)phenyl]-4,6-bis(2,4-dimethylphenyl)-1,3,5-triazine;

5-chloro-2-(2-hydroxy-3,5-di-tert-butylphenyl)-2H-benzotriazole;

2-(2-hydroxy-3-dodecyl-5-methylphenyl)-2H-benzotriazole;

5-chloro-2-(2-hydroxy-3-tert-butyl-5-methylphenyl)-2H-benzotriazole;

bis-(3-(2H-benzotriazol-2-yl)-2-hydroxy-5-tert-octyl)methane;

2-(2-hydroxy-3,5-di-tert-butylphenyl)-2H-benzotriazole;

2-(2-hydroxy-3,5-di-tert-amylphenyl)-2H-benzotriazole;

2-(2-hydroxy-3,5-di-α-cumylphenyl)-2H-benzotriazole;

2-(2-hydroxy-3-α-cumyl-5-tert-octylphenyl)-2H-benzotriazole;

2-(2-hydroxy-5-tert-octylphenyl)-2H-benzotriazole;

3-(2H-benzotriazol-2-yl)-4-hydroxy-5-(1-methylpropyl)-benzenesulfonic acid monosodium salt;

3-tert-butyl-4-hydroxy-5-(2H-benzotriazol-2-yl)-hydrocinnamic acid and sodium salt;

12-hydroxy-3,6,9-trioxadodecyl 3-tert-butyl-4-hydroxy-5-(2H-benzotriazol-2-yl)-hydrocinnamate;

octyl 3-tert-butyl-4-hydroxy-5-(2H-benzotriazol-2-yl)-hydrocinnamate;

4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);

4,6-bis(2,4-dimethylphenyl)-2-(4-octyloxy-2-hydroxyphenyl)-s-triazine;

2,4-dihydroxybenzophenone;

2,2'-dihydroxy-4,4'-dimethoxy-5,5'-disulfobenzophenone, disodium salt;

2-hydroxy-4-octyloxybenzophenone;

2-hydroxy-4-dodecyloxybenzophenone;

2,4-dihydroxybenzophenone;

2,2',4,4'-tetrahydroxybenzophenone;

4-aminobenzoic acid;

2,3-dihydroxypropyl-4-aminobenzoic acid;

3-(4-imidazolyl)acrylic acid;

2-phenyl-5-benzimidazole sulfonic acid;

N,N,N-trimethyl-α-(2-oxo-3-bornylidene)-p-toluidinium methyl sulfate;

5-benzoyl-4-hydroxy-2-methoxybenzenesulfonic acid, sodium salt;

3-(4-benzoyl-3-hydroxyphenoxy)-2-hydroxy-N,N,N-trimethyl-1-propanaminium chloride;

3-[4-(2H-benzotriazol-2-yl)-3-hydroxyphenoxy]-2-hydroxy-N,N,N-trimethyl-1-propanaminium, chloride;

2-(2-hydroxy-5-methylphenyl)-2H-benzotriazole; and 2,2'-dihydroxy-4,4'-dimethoxybenzophenone (Uvinul® 3049).

For instance, suitable UV absorbers are selected from 3-(2H-benzotriazol-2-yl)-4-hydroxy-5-(1-methylpropyl)-benzenesulfonic acid monosodium salt;

3-tert-butyl-4-hydroxy-5-(2H-benzotriazol-2-yl)-hydrocinnamic acid and sodium salt;

2-(2-hydroxy-3,5-di-tert-butylphenyl)-2H-benzotriazole;

2-(2-hydroxy-3,5-di-tert-amylphenyl)-2H-benzotriazole;

4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);

12-hydroxy-3,6,9-trioxadodecyl 3-tert-butyl-4-hydroxy-5-(2H-benzotriazol-2-yl)-hydrocinnamate;

2,4-dihydroxybenzophenone;

2,2'-dihydroxy-4,4'-dimethoxy-5,5'-disulfobenzophenone, disodium salt;

2,2',4,4'-tetrahydroxybenzophenone;

3-(4-benzoyl-3-hydroxyphenoxy)-2-hydroxy-N,N,N-trimethyl-1-propanaminium chloride;

3-[4-(2H-benzotriazol-2-yl)-3-hydroxyphenoxy]-2-hydroxy-N,N,N-trimethyl-1-propanaminium, chloride;

5-benzoyl-4-hydroxy-2-methoxy-benzenesulfonic acid, sodium salt; and 2-(2-hydroxy-3-α-cumyl-5-tert-octylphenyl)-2H-benzotriazole.

Additional suitable antioxidants are for example selected from the hindered phenolic and benzofuranone stabilizers.

Suitable antioxidants are for example selected from the group consisting of

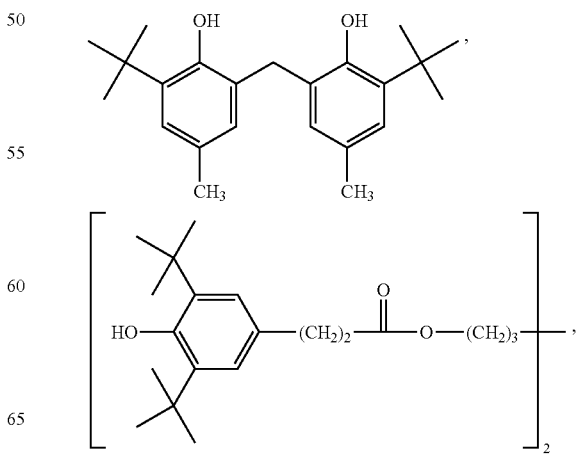

-continued
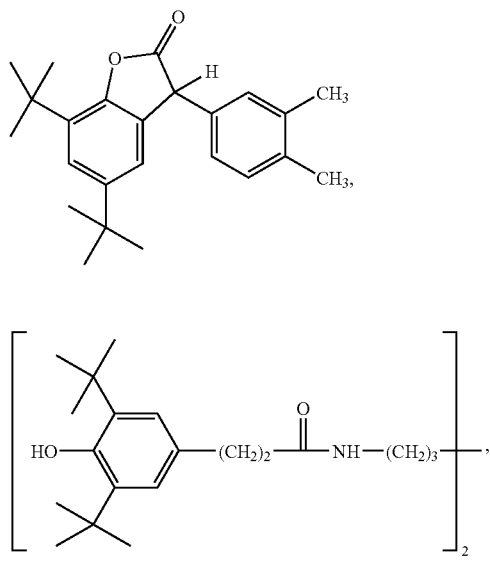
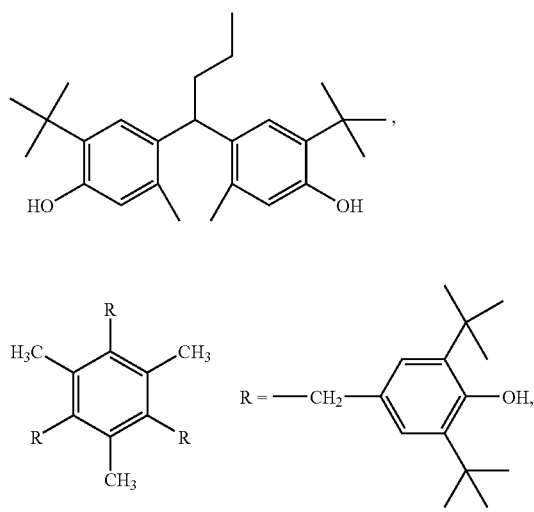
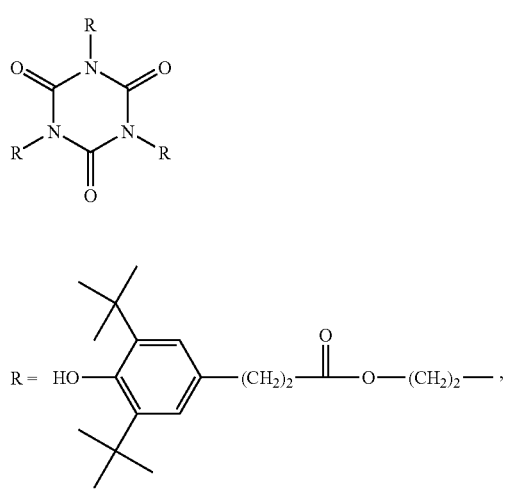
-continued
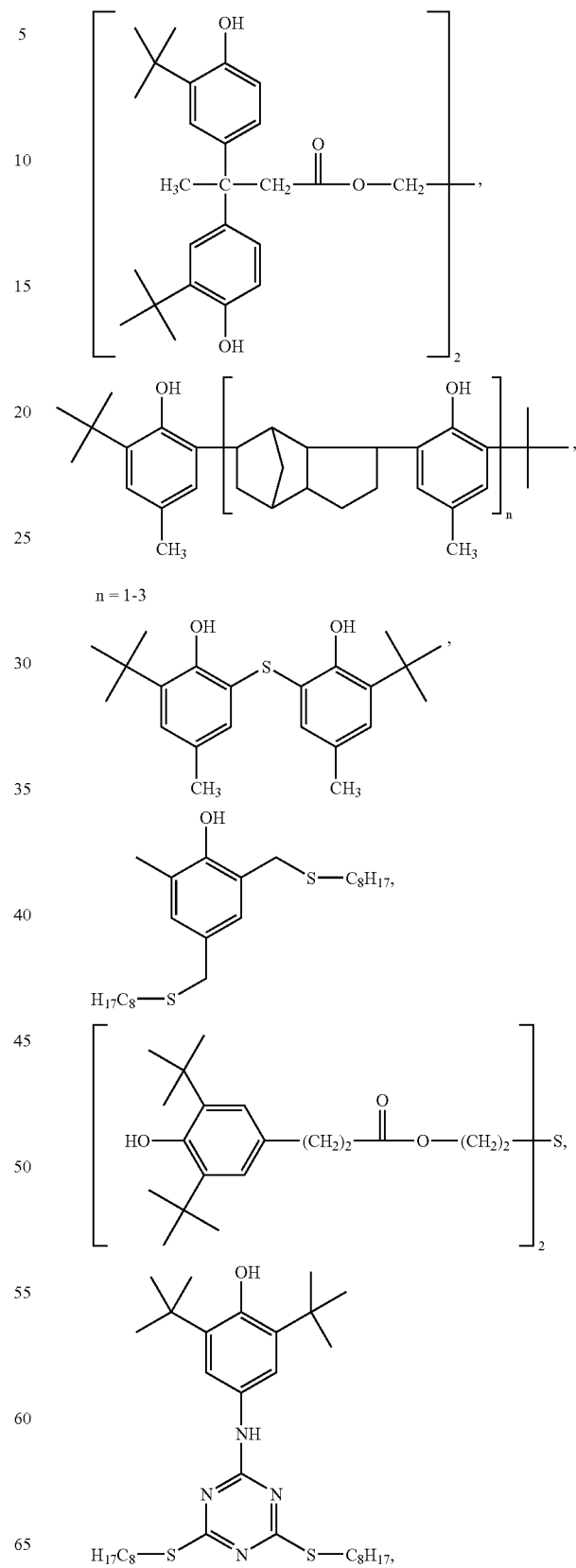
n = 1-3

-continued

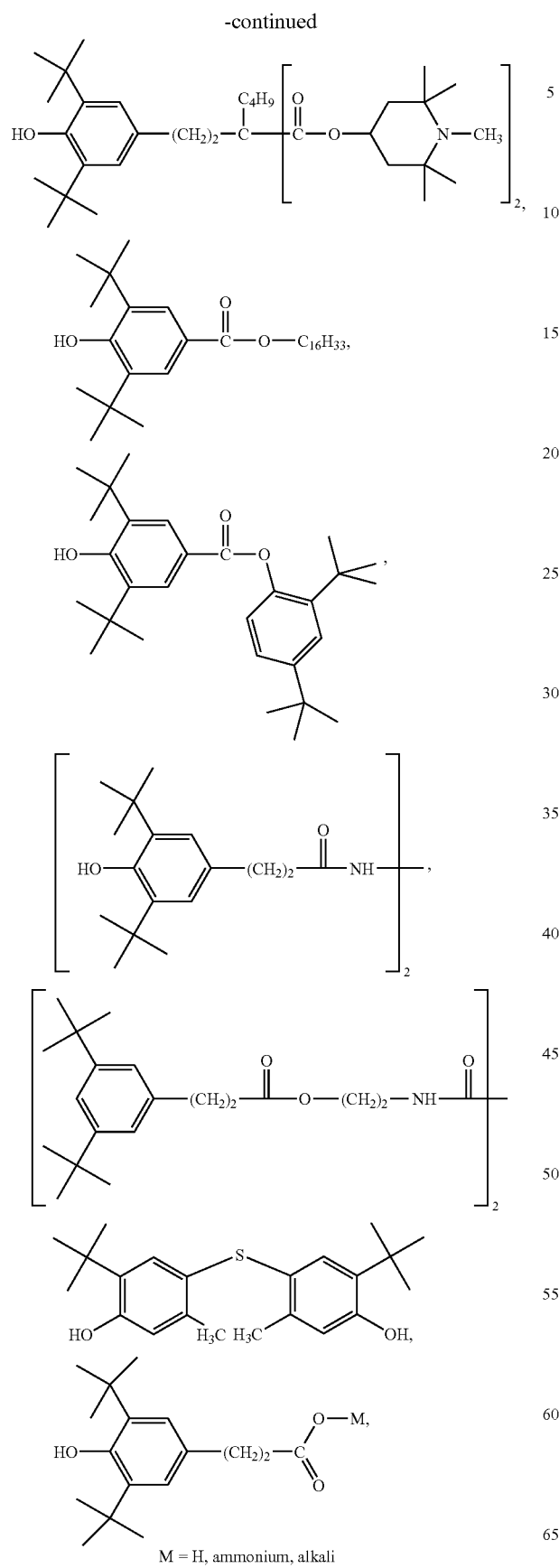

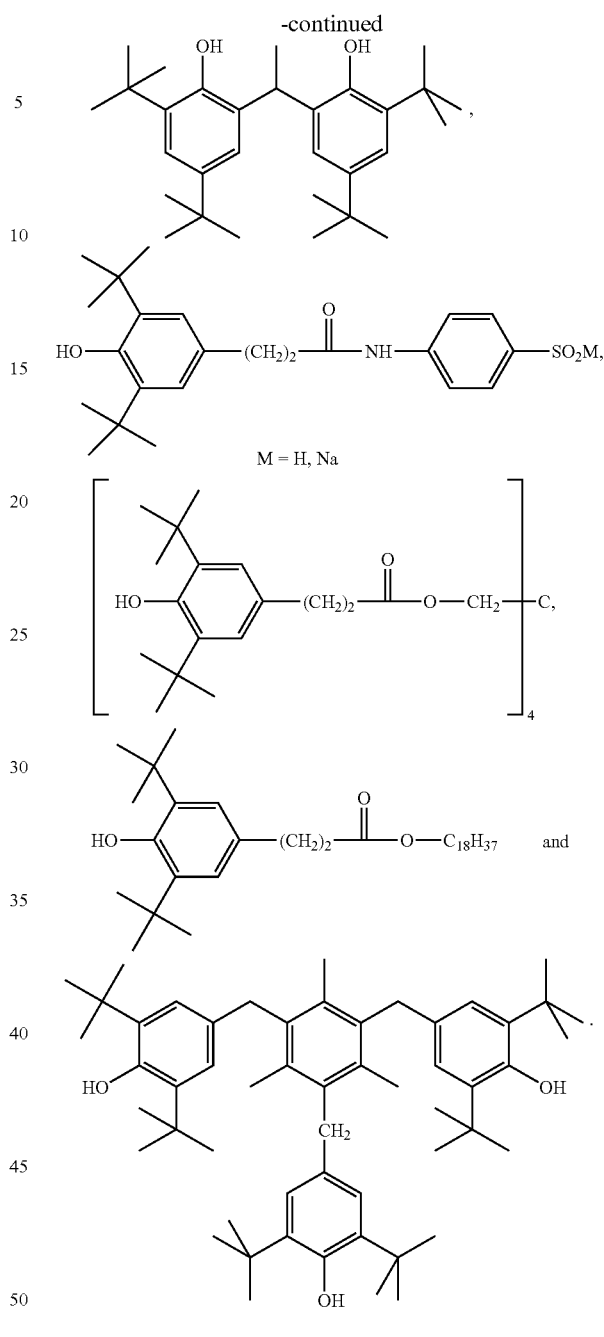

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzyl-malonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetra-methylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-amino-propylamino)ethane and 2,4,6-trichloro-1,3,5-triazine and 4-butylamino-2,2,6,6-tetramethyl-piperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

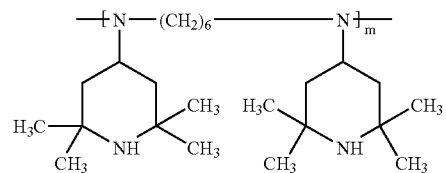

wherein m is a value from 5-50,

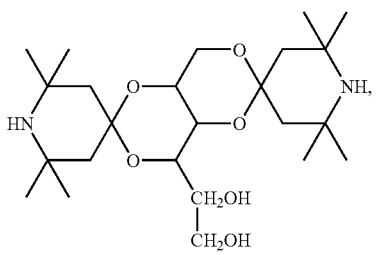

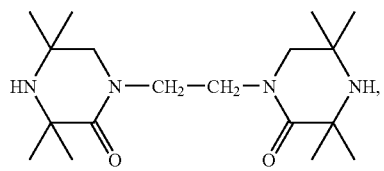

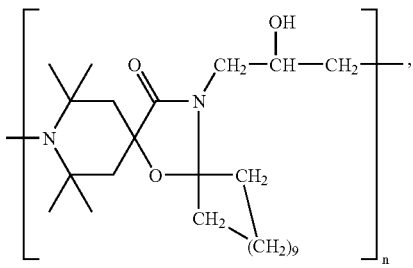

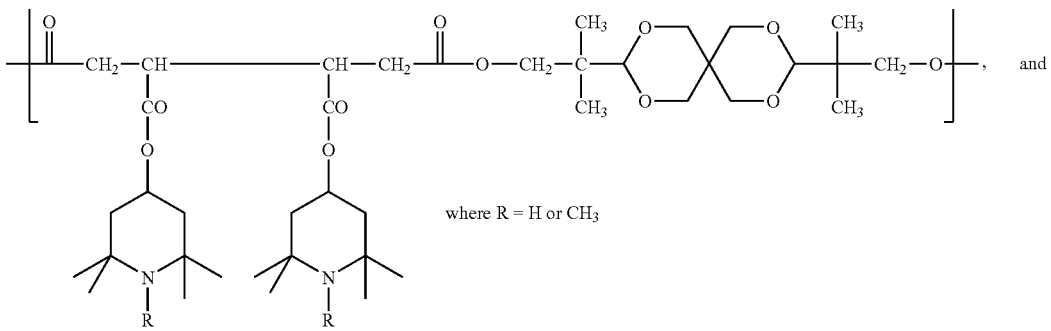

where R = H or CH₃

-continued

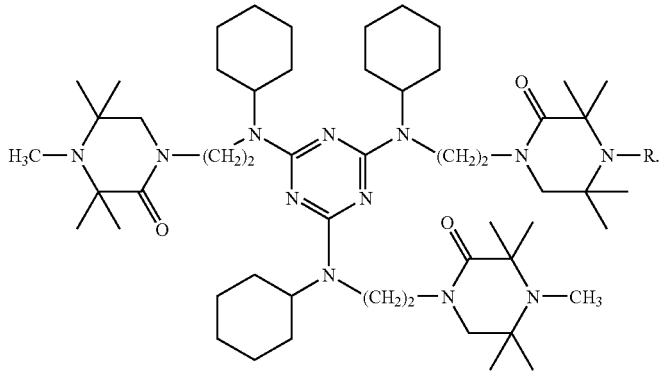

where R= H or CH$_3$

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers are for example selected from the group consisting of ethylenediaminetetracetic acid (EDTA), nitrilotriacetic acid (NTA), β-alaninediacetic acid (EDETA) or ethylenediaminedisuccinic acid (EDDS),

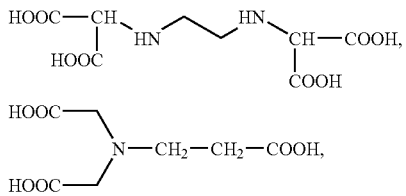

aminetrimethylenephosphoric acid (ATMP) conforming to formula

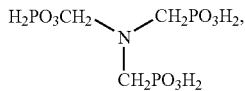

serinediacetic acid (SDA) conforming to formula

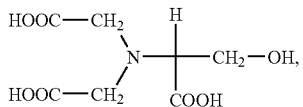

asparaginediacetic acid conforming to formula

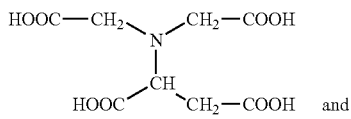 and methylglycinediacetic acid (MGDA) conforming to formula

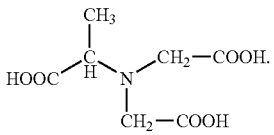

The present stabilizer systems are particularly suitable for stabilizing body care products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present body care products can be in the form of creams, ointments, pastes, foams, gels, lotions, powders, make-ups, sprays, sticks or aerosols. The present stabilizer systems may be present in the oil phase or in the aqueous or aqueous/alcoholic phase.

The additives of component (b) are present, for example, in the body care and household products in a concentration of about 5 to about 10000 ppm, based on the total formulation, for example from about 10 to about 5000 ppm, for example from about 100 to about 1000 ppm. For example the additives of component (b) are present in the body care and household products in a concentration of about 5, 10, 15, 20, 25, 35, 40, 45 or 50 ppm, based on the total formulation. For example, the additives of component (b) are present from about 5 to about 1000 ppm in the formulations (compositions) of this invention. These ppm concentrations are parts by weight.

Laundry detergents, fabric softeners or other products, from which the additives of component (b) are intended for deposition onto fabrics with use, are considered household products of this invention, and the above concentration levels also pertain thereto. The present additives of component (b) are effective at stabilizing the laundry detergents and fabric softeners, as well as the fabrics treated therewith.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropylmyristate or beeswax and/or hydrocarbon compounds, such as paraffin oil. Suitable emulsifiers are surfactants having primarily hydrophilic properties, such as the corresponding nonionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturisers and wetting agents, such as polyoxyethylenesobitan fatty acid ester. The gels furthermore contain commercially available preservatives, such as benzyl alcohol, phenethyl alcohol, phenoxyethanol and the like.

The following is a list of examples of body care products of this invention and their ingredients:

| Body care product | Ingredients |
| --- | --- |
| moisturizing cream | vegetable oil, emulsifier, thickener, perfume, water, antioxidant, UV absorbers |
| shampoo | surfactant, emulsifier, preservatives, perfume, antioxidant, UV absorbers |
| toothpaste | cleaning agent, thickener, sweetener, flavor, colorant, antioxidant, water, UV absorbers |
| lip-care stick | vegetable oil, wax, $TiO_2$, antioxidant, UV absorbers |

The present body care products, household products, textiles and fabrics have high stability towards color changes and chemical degradation of the ingredients present in these products. For example, present compositions that comprise a dye are found to have excellent color stability.

Accordingly, the present invention further pertains to a stabilized composition comprising
(a) a body care product, household product, textile or fabric,
(b) an effective stabilizing amount of at least one compound selected from the group consisting of
(i) the dialkylhydroxylamine stabilizers,
(ii) the dialkylhydroxylamine stabilizer salts,
(iii) the nitrone stabilizers and
(iv) the amine oxide stabilizers and
(d) a dye.

The term "effective stabilizing amount" means for example the amount necessary to achieve the desired dye stability.

Dyes according to the present invention are for example:
inorganic pigments, for example iron oxide (Iron Oxide Red, Iron Oxide Yellow, Iron Oxide Black, etc.), Ultramarines, Chromium Oxide Green or Carbon Black;
natural or synthetic organic pigments;
disperse dyes which may be solubilzed in solvents like direct hair dyes of the HC type, for example HC Red No. 3, HC Blue No. 2 and all other hair dyes listed in International Cosmetic Ingredient Dictionary and Handbook, 7$^{th}$ edition 19997) or the dispersion dyes listed in Color Index International or Society of Dyers and Colourists;
color varnishes (insoluble salts of soluble dyes, like many Ca-, Ba- or Al-salts of anionic dyes);
soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wavelength of ca. 4000 to 700 nm). The absorption is often caused by the following chromophores: Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present stabilizer systems are also used in household cleaning and treatment agents, for example in laundry products and fabric softeners, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

The present invention also concerns home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

The stabilizers of the present invention may be employed in fabric treatment that takes place after use of the fabric, referred to as fabric care. Such treatments include laundering, which uses detergents and/or fabric conditioner, and the application of non-detergent based fabric care products, such as spray-on products. When employed in this fashion, the present stabilizers are intended for deposition onto the fabric and used to protect the fabric, colorants and fragrances associated with said these fabrics from environmental damage.

Typical examples of household cleaning and treating agents are:

| Household cleaners/household treating agents | Ingredients |
|---|---|
| detergent concentrate | surfactant mixture, ethanol, antioxidant, water, UV absorbers, antioxidant |
| shoe polish | wax, wax emulsifier, antioxidant, water, preservative, UV absorbers, antioxidant |
| wax-containing floor cleaning agent | emulsifier, wax, sodium chloride, antioxidant, water, preservative, UV absorbers, antioxidant |

The present stabilizers are for example incorporated by dissolution in an oil phase or alcoholic or water phase, where required at elevated temperature.

The present invention also pertains to a method of stabilizing a body care product, household product, textile or fabric, which comprises incorporating therein or applying thereto at least one compound selected from the group consisting of (i) the dialkylhydroxylamine stabilizers,
(ii) the dialkylhydroxylamine stabilizer salts,
(iii) the nitrone stabilizers and
(iv) the amine oxide stabilizers.

In the case of stabilized fabrics, for example dyed fabrics, the present stabilizers are applied thereto via deposition from for instance detergents, fabric conditioners or non-detergent based fabric care products.

The present fabrics are natural or synthetic, and may be woven or nonwoven.

The present invention also pertains to a method of stabilizing a body care product, household product, textile or fabric, each of which contain a dye, which comprises incorporating therein or applying thereto at least one compound selected from the group consisting of components (i)-(iv). The present stabilizers of components (i)-(iv) are very effective towards the stabilization of dyes in the present compositions.

The textiles of this invention are for example textile fiber materials, for example nitrogen-containing or hydroxy-group-containing fiber materials, for instance textile fiber materials selected from cellulose, silk, wool, synthetic polyamides, leather and polyurethanes. Included are cotton, linen and hemp, pulp and regenerated cellulose. Included also are cellulosic blends, for example mixtures of cotton and polyamide or cotton/polyester blends.

The additives of the present invention are for example applied to textiles in a dyeing or printing process, or in a finishing process. For instance, the additives may be applied as part of a dye formulation. The additives may be applied to textiles for example in an ink-jet printing process. The additives are for example applied as part of an aqueous dye solution or printing paste. They may be applied in an exhaust method or dyeing by the padder dyeing method, in which the textiles are impregnated with aqueous dye solutions, which may contain salts, and the dyes and additives are fixed, after an alkali treatment or in the presence of alkali, if appropriate with the action of heat or by storage at room temperature for several hours. After fixing, the dyeings or prints are rinsed thoroughly with cold and hot water, if appropriate with the addition of an agent which has a dispersing action and promotes diffusion of the non-fixed portions.

The dye or ink formulations for application to textiles may comprise further customary additves, for example surfactants, antifoams, antimicrobials and the like, for example as disclosed in U.S. Pat. Nos. 6,281,339, 6,353,094 and 6,323,327, the disclosures of which are hereby incorporated by reference.

The following Examples illustrate the invention. Percentages are in weight percent unless indicated otherwise.

EXAMPLE 1

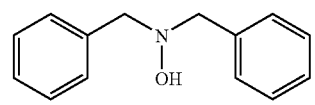

The instant compound is obtained from Aldrich Chemical Company.

EXAMPLE 2

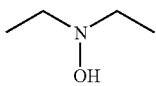

The instant compound is obtained from Aldrich Chemical Company.

EXAMPLE 3

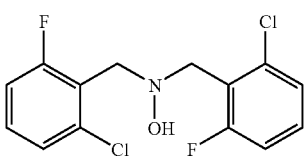

The instant compound is obtained from Aldrich Chemical Company.

EXAMPLE 4

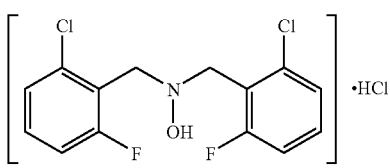

Example 3 (3.2 g, 0.012 mole) is dissolved in 50 mL of anhydrous isopropanol. To this stirred solution is added dropwise 1.5 mL of absolute isopropanol (7.60 molar hydrochloric acid) at 40 C. After thirty minutes, the mixture is heated to 50 C for thirty minutes. The resulting clear solution is cooled to 5 C. The resulting white precipitate is filtered, washed with cold isopropanol, and dried to constant weight in a vacuum oven. The title compound is received (3.4 g, 92% yield) as a white solid with a melting point of 161-169° C. whose structure is consistent with HNMR.

EXAMPLE 5

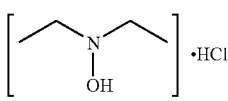

Example 2 (8.9 g, 0.1 mole) is dissolved in 100 mL of anhydrous diethylether. To this stirred solution is added dropwise 59 mL of absolute ethanol (1.68 molar hydrochloric acid) at ambient temperature. After three hours, the solvent is removed by distillation and replaced with 25 mL of isopropanol/hexane (1:2 ratio). The resulting white precipitate is filtered, washed with cold isopropanol/hexane (1:2 ratio), and dried to constant weight in a vacuum oven. The title compound is received (5.2 g, 43% yield) as a white solid with a melting point of 70-72 C whose structure is consistent with HNMR.

EXAMPLE 6

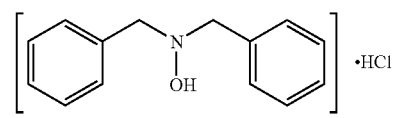

Example 1 (10.7 g, 0.05 mole) is dissolved in 35 mL of heptane and 35 mL of anhydrous isopropanol. To this stirred solution is added dropwise 9.38 g of absolute isopropanol containing 0.05 mole of hydrochloric acid at ambient temperature. The resulting white precipitate is filtered, recrystallized from 400 g of boiling isopropanol, and dried to constant weight in a vacuum oven. The title compound is received (8.5 g, 68% yield) as a white solid with a melting point of 174 C whose structure is consistent with HNMR.

EXAMPLE 7

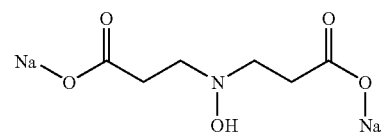

The instant compound is prepared according to J. E. Baldwin, *Tetrahedron*, 1984, 40(21), 4363-70.

EXAMPLE 8

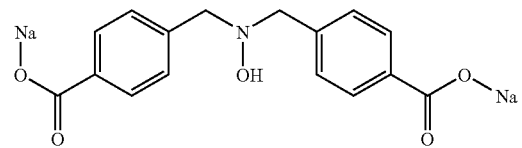

The instant compound is prepared according to J. E. Baldwin, *Tetrahedron*, 1984, 40(21), 4363-70.

EXAMPLE 9

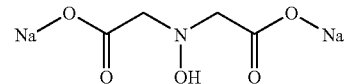

The instant compound is prepared according to J. E. Baldwin, *Tetrahedron*, 1984, 40(21), 4363-70.

EXAMPLE 10

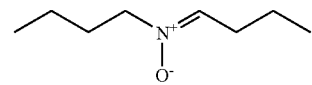

The instant compound is prepared according to U.S. Pat. No. 4,898,901.

EXAMPLE 11

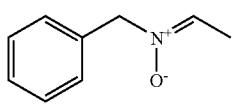

The instant compound is prepared according to U.S. Pat. No. 4,898,901.

EXAMPLE 12

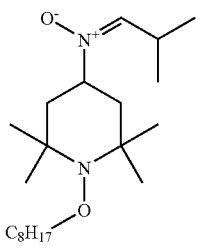

The instant compound is prepared according to U.S. Pat. Nos. 4,972,009 and 5,202,441.

EXAMPLE 13

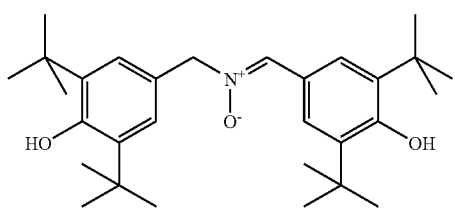

The instant compound is prepared according to U.S. Pat. No. 4,898,901.

EXAMPLE 14

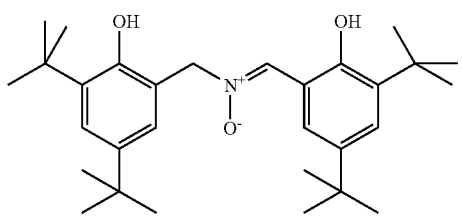

The instant compound is prepared according to U.S. Pat. No. 4,898,901.

EXAMPLE 16

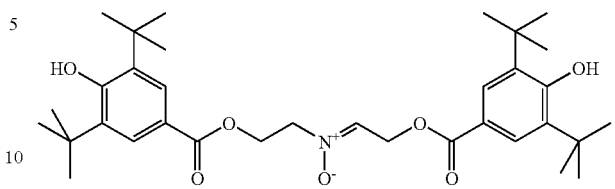

The instant compound is prepared according to U.S. Pat. No. 4,898,901.

EXAMPLE 17

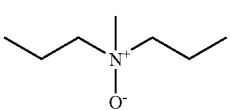

The instant compound is prepared according to U.S. Pat. Nos. 5,081,300, 5,162,408, 5,844,029, 5,880,191, and 5,922,794.

EXAMPLE 18

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Suave® Natural Fresh Mountain Strawberry Shampoo) with agitation. The stabilized shampoo formulation is agitated for 15 minutes and put into 20 mL glass scintillation vials. These formulations are weathered under fluorescent light aging at ambient temperature. The CIEL *a*b coordinates before and after exposure are measured using X-Rite 938 Spectrodensitometer. Color change is expressed as Delta E (DE). The color change is given by Delta E (DE) which is calculated by:

$$DE=[(DL^*)^2+(Da^*)^2+(Db^*)^2]^{1/2}$$

| Stabilizer (loading at 0.30 wt %) | DE after 2 weeks |
| --- | --- |
| None | 8.49 |
| Example 9 | 7.38 |
| Example 2 | 7.26 |
| Example 5 | 6.44 |
| Example 7 | 5.13 |
| Example 6 | 4.61 |
| Example 8 | 4.46 |

The compounds according to this invention are able to improve clearly the light fastness of shampoo formulations.

EXAMPLE 19

The instant compounds are added to a commercial shampoo formulation and are evaluated for their ability to reduce the amount of dye fading when the samples are exposed to fluorescent lighting. The instant compounds (0.36 g) are dissolved in 5 mL of methanol which is then added to 120 g of shampoo (Clairol® Herbal Essences Shampoo) with agitation. The stabilized shampoo formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer (loading at 0.30 wt %) | DE after 2 weeks |
| --- | --- |
| None | 1.86 |
| Example 8 | 1.40 |
| Example 5 | 1.22 |

The compounds according to this invention are able to improve clearly the light fastness of shampoo formulations.

EXAMPLE 20

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Scope® Original Mint) with agitation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer (loading at 0.30 wt %) | DE after 2 weeks |
| --- | --- |
| None | 5.30 |
| Example 5 | 5.02 |
| Example 8 | 2.28 |

The compounds according to this invention are able to improve clearly the light fastness of mouthwash formulations.

EXAMPLE 21

The instant compounds are added to a commercial mouthwash formulation and are evaluated for their ability to reduce the amount of dye fading when the samples are exposed to fluorescent lighting. The instant compounds (0.36 g) are dissolved in 5 mL of methanol which is then added to 120 g of mouthwash (Listerine® Cool Mint) with agitation. The stabilized mouthwash formulation is agitated for 15 minutes and put into 20 mL glass scintillation vials. These formulations are weathered under fluorescent light aging at ambient temperature. The CIEL*a*b coordinates before and after exposure are measured using X-Rite 938 Spectrodensitometer. Color change is expressed as Delta E (DE).

| Stabilizer (loading at 0.30 wt %) | DE after 7 weeks |
| --- | --- |
| None | 2.70 |
| Example 9 | 2.64 |
| Example 8 | 2.04 |
| Example 5 | 0.91 |
| Example 2 | 0.64 |

The compounds according to this invention are able to improve clearly the light fastness of mouthwash formulations.

EXAMPLE 22

The instant compounds are added to a commercial shampoo formulation and are evaluated for their ability to reduce the amount of dye fading when the samples are exposed to fluorescent lighting. The instant compounds are dissolved in a shampoo formulation with agitation. 3-(2H-benzotriazol-2-yl)-4-hydroxy-5-(1-methylpropyl)-benzenesulfonic acid monosodium salt, a benzotriazole UV absorber, is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

EXAMPLE 23

The instant compounds are added to a commercial shampoo formulation and are evaluated for their ability to reduce the amount of dye fading when the samples are exposed to fluorescent lighting. The instant compounds are dissolved in a shampoo formulation with agitation. A s-triazine UV absorber is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

EXAMPLE 24

The instant compounds are added to a commercial shampoo formulation and are evaluated for their ability to reduce the amount of dye fading when the samples are exposed to fluorescent lighting. The instant compounds are dissolved in a shampoo formulation with agitation. A benzophenone UV absorber is added to the shampoo formulation. These formulations are weathered under fluorescent light at ambient temperature. The CIEL*a*b coordinates before and after exposure are measured. The change in color is expressed by Delta E (DE). The compounds according to this invention are quite efficacious in improving light fastness of shampoo formulations.

EXAMPLE 25

The instant compounds are added to a commercial mouthwash formulation and are evaluated for their ability to reduce the amount of dye fading when the samples are exposed to fluorescent lighting. The instant compounds are added to a mouthwash formulation with agitation. 3-(2H-benzotriazol-2-yl)-4-hydroxy-5-(1-methylpropyl)-benzene-sulfonic acid monosodium salt, a benzotriazole UV absorber, is added to the mouthwash formulation. These formulations are weathered under fluorescent lighting at ambient temperature. The CIEL*a*b coordinates before and after exposure are measured. Color change is expressed as Delta E (DE). The compounds according to this invention are quite efficacious in improving light fastness of mouthwash formulations.

EXAMPLE 26

The instant compounds are added to a commercial mouthwash formulation and are evaluated for their ability to reduce the amount of dye fading when the samples are exposed to fluorescent lighting. The instant compounds are added to a mouthwash formulation with agitation. An s-triazine UV absorber is added to the mouthwash formulation. These formulations are weathered under fluorescent lighting at ambient temperature. The Cl EL*a*b coordinates before and after exposure are measured. Color change is expressed as Delta E (DE). The compounds according to this invention are quite efficacious in improving light fastness of mouthwash formulations.

EXAMPLE 27

The instant compounds are added to a commercial mouthwash formulation and are evaluated for their ability to reduce the amount of dye fading when the samples are exposed to fluorescent lighting. The instant compounds are added to a mouthwash formulation with agitation. A benzophenone UV absorber is added to the mouthwash formulation. These formulations are weathered under fluorescent lighting at ambient temperature. The CIEL*a*b coordinates before and after exposure are measured. Color change is expressed as Delta E (DE). The compounds according to this invention are quite efficacious in improving light fastness of mouthwash formulations.

EXAMPLE 28

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR BLUE ABL9 (FD&C Blue No. 1)

About 20 mL of each of the aqueous test formulations are placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 29

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR RED ARE33 (FD&C Red No. 33).

About 20 mL of each of the aqueous test formulations are placed in a borosilicate glass bottle. The glass bottles are exposed in an Atlas Ci-65 Xenon arc WeatherOmeter, AATCC Test Method 16, option E. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 30

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is FD&C Red No. 40.

About 20 mL of each of the aqueous test formulations are placed in a borosilicate glass bottle. The glass bottles are exposed in an Atlas Ci-65 Xenon arc WeatherOmeter, AATCC Test Method 16. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 31

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR BLUE ABL9 (FD&C Blue No. 1)

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 32

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is PURICOLOR RED ARE33 (FD&C Red No. 33).

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 33

An aqueous based test formulation is prepared as follows:

| | |
|---|---|
| sodium laureth sulfate (30%, TEXAPON NSO, Cognis) | 30% |
| cocamidopropylbetaine (30%, DEHYTON K, Cognis) | 10% |
| colorant* | 0.001% |
| instant stabilizer | 0.05% |
| citric acid (10% aqueous solution) | to pH 6 |
| deionized water | to 100% |

*Colorant is FD&C Red No. 40.

About 20 mL of each of the aqueous test formulations are placed in a borosilicate glass bottle. The glass bottles are also exposed to accelerated fluorescent lighting, Philips, 40 Watt, Daylight Deluxe (D65), full exposure to light. Color measurements are performed on a Hunter Ultrascan XE spectrophotometer. Delta L, a and b values are the difference between the initial values and the values at each interval. It is seen that the stabilizers of the present invention provide excellent color stability in personal care products.

EXAMPLE 34

Moisturizer Cream

The components of phase A are thoroughly mixed in a homogenizer for 10 min at 75-80° C. The water phase B, likewise heated to 75-80° C. beforehand, is slowly added and the mixture is homogenized for 1 min. The mixture is cooled, with stirring, to 40° C. and then phases C and E are added and the mixture is homogenized for 1 min. Subsequently, phase D is added and the mixture is homogenized for ½ min and cooled, with stirring, to room temperature.

| Phase | Ingredients | (w/w) % |
|---|---|---|
| A | passionflower oil | 8 |
| | glyceryl dioleate | 4 |
| | dicapryl ether | 4 |

-continued

| Phase | Ingredients | (w/w) % |
|---|---|---|
| | Isopropylisostearate | 4 |
| | instant stabilizer | 0.05 |
| B | water, demin. | ad. 100 |
| | EDTA | 0.1 |
| C | Carbomer | 0.15 |
| D | sodium hydroxide | 10% |
| | | 0.20 |
| E | perfume; preservative | q.s. |

It is seen that the stabilizers of the present invention provide excellent color stability in personal care products.

EXAMPLE 35

Toilet Water

The components below are thoroughly mixed in the cited sequence at 50° C., a clear homogeneous solution being obtained. The UV absorber is, for example, 3-(2H-benzotriazol-2-yl)-4-hydroxy-5-(1-methylpropyl)-benzenesulfonic acid monosodium salt.

| Ingredients | (w/w) % |
|---|---|
| ethanol, 96% | 60 |
| d-limonene | 5 |
| cedrene | 1.5 |
| citronellol | 0.5 |
| savin | 0.5 |
| instant stabilizer | 0.08 |
| UV absorber | 0.1 |
| S,S-EDDS | 0.005 |
| colorant (D&C Yellow No. 5) | 0.02 |
| water | ad. 100 |

Excellent results are achieved for this example of a toilet water formulation.

EXAMPLE 36

Hair Styling Spray

The hydroxypropyl cellulose is first predissolved in half of the alcohol (Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved. The UV absorber used is, for example, benzophenone-4 is 5-benzoyl-4-hydroxy-2-methoxybenzenesulfonic acid, sodium salt.

| Ingredients | (w/w) % |
|---|---|
| alcohol, anhydrous | 96.21 |
| octylacrylamide/acrylate/ butylaminoethylmethacrylate copolymer | 2.52 |
| hydroxypropyl cellulose | 0.51 |
| aminomethylpropanol (95%) | 0.46 |
| instant stabilizer | 0.05 |
| UV absorber | 0.05 |
| perfume oil | 0.20 |

Excellent results are achieved for this example of a hair styling spray formulation.

EXAMPLE 37

Shampoo for Greasy Hair

The components listed below are mixed, with stirring, at room temperature until they are completely dissolved. The pH is 6.5. The UV absorber is, for example, 2-(2-hydroxy-3-dodecyl-5-methylphenyl)-2H-benzotriazole.

| Ingredients | (w/w) % |
| --- | --- |
| sodium myreth sulfate | 50.00 |
| TEA abietoyl collagen hydrolysate | 3.50 |
| laureth-3 | 3.00 |
| colorant (D&C Red No. 33) | 0.20 |
| instant stabilizer | 0.05 |
| UV absorber | 0.15 |
| phosphonomethylchitosan, sodium salt | 0.01 |
| perfume oil | 0.10 |
| water | ad. 100 |

Excellent results are achieved for this example of a shampoo composition for oily hair.

EXAMPLE 38

Leather Dressing and Cleaning Agent

The stabilizer is predissolved in the terpene. The components are then stirred in the cited sequence at about 65° C. until homogeneous. The mixture is then cooled to room temperature.

| Ingredients | (w/w) % |
| --- | --- |
| synthetic soap (Zetesap 813) | 7.85 |
| Glycerol | 6.00 |
| anionic surfactant (Lumorol 4192; Mulsifan RT 13) | 22.00 |
| Vaseline | 11.00 |
| paraffin 52/54 | 20.00 |
| Talcum | 2.00 |
| orange terpene | 4.00 |
| instant stabilizer | 0.02 |
| Water | 27.13 |

Excellent results are achieved for this example of a leather dressing and cleaning agent composition.

EXAMPLE 39

Glass Detergent

The components listed below are dissolved in the cited sequence until a clear homogeneous mixture is obtained.

| Ingredients | (w/w) % |
| --- | --- |
| anionic/amphoteric surfactants (Lumorol RK) | 0.7 |
| butyl glycol | 5.0 |
| Isopropanol | 20.0 |
| d-limonene | 4.00 |
| instant stabilizer | 0.02 |
| water, demin. | ad. 100 |

Excellent results are achieved for this example of a glass detergent formulation.

EXAMPLE 40

Protection of Dyes in Fabrics

The instant stabilizers are each deposited (from water) on a dyed cotton fabric at 0.05, 0.1, 0.2, 0.5 and 1.0 percent by weight, based on the weight of the cotton. The dyed fabrics contain the following dyes at 0.05, 0.1, 0.2 and 0.5 percent by weight based on cotton. This results in 60 separate formulations for each dye listed:

Scarlet HE-3G

Crimson HE-XL

Yellow HE-6G

Red HE-XL

Blue HE-XL

Turquoise H-A

Navy HE-XL

Remazol

Red RB

Brilliant Red RBS

Orange FR

Navy CG

Turquoise G

Black B

The cotton fabrics are subjected to light exposure in an Atlas Ci-65 Xenon arc WetherOmeter or to accelerated fluorescent lighting. The present stabilizers provide outstanding color protection to the dyed fabrics. This experiment simulates dye protection achievable through deposition of the present stabilizers via treatment with, for example, stabilizer-containing laundry detergent or fabric conditioner.

EXAMPLE 41

Protection of Dyes in Fabrics

The instant stabilizers and UV absorbers, for example 3-(2H-benzotriazol-2-yl)-4-hydroxy-5-(1-methylpropyl)-benzenesulfonic acid monosodium salt, are each deposited (from water) on a dyed cotton fabric at 0.05, 0.1, 0.2, 0.5 and 1.0 percent by weight, based on the weight of the cotton. The dyed fabrics contain the following dyes at 0.05, 0.1, 0.2 and 0.5 percent by weight based on cotton. This results in 60 separate formulations for each dye listed:

Scarlet HE-3G

Crimson HE-XL

Yellow HE-6G

Red HE-XL

Blue HE-XL

Turquoise H-A

Navy HE-XL

Remazol

Red RB

Brilliant Red RBS

Orange FR

Navy CG

Turquoise G

Black B

The cotton fabrics are subjected to light exposure in an Atlas Ci-65 Xenon arc WetherOmeter or to accelerated fluorescent lighting. The present stabilizers provide outstanding color protection to the dyed fabrics. This experiment simulates dye protection achievable through deposition of the present stabilizers via treatment with for example stabilizer-containing laundry detergent or fabric conditioner.

What is claimed is:

1. A stabilized composition comprising
   (a) a body care product, household cleaning agent, or household treating agent selected from the group consisting of skin-care products, bath and shower products, liquid soaps, bar soaps, preparations containing fragrances and odoriferous substances, hair-care products, dentrifices, deodorizing and antiperspirant preparations, decorative preparations, hormone preparations, vitamin preparations, vegetable extract preparations, antibacterial preparations, laundry detergents and fabric softeners, non-detergent based fabric care products, liquid cleansing and scouring agents, glass detergents, neutral cleaners, all-purpose cleaners, acid household cleaners, bathroom cleaners, dishwashing agents, kitchen and oven cleaners, clear rinsing agents, dishwasher detergents, shoe polishes, polishing waxes, floor detergents and polishes, metal, glass, and ceramic cleaners, fabric care products, rug cleaners and carpet shampoos, agents for removing rust, furniture and multipurpose polishes, leather and vinyl dressing agents, and solid and liquid air fresheners, and
   (b) from about 5 ppm to about 10000 ppm based on the total composition of at least one compound selected from dialkylhydroxylamine stabilizer salts,
   said dialkylhydroxylamine stabilizer salts are of the formula $(R_1R_2N—OH).(HY)$ where
   $R_1$ is alkyl of 1 to 36 carbon atoms, cycloalkyl of 5 to 12 carbon atoms or aralkyl of 7 to 9 carbon atoms; or $R_1$ is said alkyl, cycloalkyl or aralkyl substituted by one to six alkyl of 1 to 12 carbon atoms, halogen, cyano, $E_1O—$, $E_1CO—$, $E_1OCO—$, $E_1COO—$, $E_1S—$, $E_1SO—$, $E_1SO_2—$, $—NH_2$, $—NHE_1$, $—NE_1E_2$, $—PO(OE_1)(OE_2)$ or $—OPO(OE_1)(OE_2)$ groups;
   $R_2$ is hydrogen or independently has the same meaning as $R_1$, where at least one of $R_1$ and $R_2$ contains a hydrogen alpha to the —NOH moiety; or
   $R_1$ and $R_2$ together form a $C_{2-12}$ heterocyclic ring which contains at least one carbon substituted hydrogen alpha to the —NOH moiety, where said $C_{2-12}$ heterocyclic ring is unsubstituted or is substituted by one to three three alkyl of 1 to 12 carbon atoms, halogen, cyano, $E_1O—$, $E_1CO—$, $E_1OCO—$, $E_1COO—$, $E_1S—$, $E_1SO—$, $E_1SO_2—$, $—NH_2$, $—NHE_1$, $—NE_1E_2$, $—PO(OE_1)(OE_2)$ or $—OPO(OE_1)(OE_2)$ groups; or where said $C_{2-12}$ heterocyclic ring is interrupted by one to three $—O—$, $—NE_1-$, $—CO—$, $—CONE_1-$, $—S—$, $—SO—$, $—SO_2—$, $—COO—$, $—PO_3—$ or $—PO_4E_1$ groups; or where said heterocyclic ring is both substituted and interrupted by said groups;
   $E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500; and
   HY is an inorganic or organic acid
   wherein Y is selected from the group consisting of phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, a carboxylate of nitrilotriacetic acid (NTA), a carboxylate of diethylenetriaminepentamethylenephosphonic acid (DTPMPA), a carboxylate of hydroxyethylethytenediamine-triacetic acid (HEDTA), a carboxylate of ethylenediaminetetraacetic acid (EDTA), a carboxylate of diethylenetriaminepentaacetic acid (DTPA), diethylenediaminetetraacetic acid, a carboxylate of diethylenetriaminepentaacetic acid, an alkylsulfonate, and an arylsulfonate.

2. A composition according to claim 1 where Y is chloride, bisulfate, sulfate, phosphate, nitrate, ascorbate, formate, acetate, benzoate, oxalate, citrate, a carboxylate of ethylenediaminetetraacetic acid a carboxylate of diethylenetriaminepentaacetic acid or polyacrylate.

3. A composition according to claim 1 where Y is chloride, bisulfate or citrate.

4. A composition according to claim 1 in which the dialylhydroxylamine stabilizer salts are selected from the group consisting of HY salts of N,N-dibenzylhydroxylamine, N,N-dimethyl-hydroxylamine, N,N-diethylhydroxylamine, N,N-bis(2-hydroxypropyl)hydroxylamine, N,N-bis(3-hydroxypropyl)hydroxylamine, N,N-bis(2-carboxyethyl)-hydroxylamine, N,N-bis(benzylthio-methyl)hydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine, N,N-di(hydrogenated tallow) hydroxylamine,

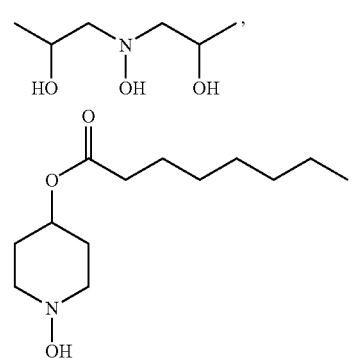

and

-continued

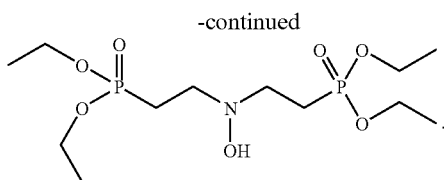

5. A composition according to claim 1 in which the dialkylhydroxylamine stabilizer salts are HY salts of N,N-diethylhydroxylamine, N,N-bis(2-hydroxypropyl)hydroxylamine, N,N-bis(3-hydroxypropyl)hydroxylamine or N,N-dibenzylhydroxylamine or N,N-di(hydrogenated tallow) hydroxylamine.

6. A composition according to claim 1 in which the dialkylhydroxylamine stabilizer salts are HY salts of N,N-diethylhydroxylamine or N,N-dibenzylhydroxylamine.

7. A composition according to claim 1 further comprising (c) at least one compound selected from the group consisting of ultraviolet light absorbers, antioxidants, tocopherol, tocopherol acetate, hindered amine light stabilizers, complex formers, optical brighteners, surfactants, and polyorganosiloxanes.

8. A composition according to claim 7 where the ultraviolet light absorbers are selected from the group consisting of 2H-benzotriazoles, s-triazines, benzophenones, α-cyanoacrylates, oxanilides, benzoxazinones, benzoates and α-alkyl cinnamates.

9. A composition according to claim 1 further comprising (d) a dye.

10. A composition according to claim 1 where the dialkylhydroxylamine salt compounds are present in a concentration of about 10 ppm to about 5000 ppm based on the total composition.

11. A composition according to claim 1 wherein the skin-care products are selected from the group consisting of body oils, body lotions, body gels, treatment creams, skin protection ointments, shaving preparations and skin powders.

12. A composition according to claim 1 wherein the preparations containing fragrances and odoriferous substances are selected from the group consisting of scents, perfumes, toilet waters and shaving lotions.

13. A composition according to claim 1 wherein the hair-care products are selected from the group consisting of shampoos, hair conditioners, 2 in 1 conditioners, leave in and rinse off conditioners, agents for styling and treating hair, perming agents, relaxants, hair sprays and lacquers, hair dyeing systems, permanent, demi-permanent, semi-permanent and temporary hair dyeing systems, and hair bleaching agents.

14. A composition according to claim 1 wherein the decorative preparations are selected from the group consisting of lipsticks, nail varnishes, eye shadows, mascaras, dry and moist make-up, rouge, powders, depilatory agents, sun care and after sun products.

* * * * *